United States Patent [19]

Ullman et al.

[11] 4,215,104
[45] Jul. 29, 1980

[54] MULTI-FRACTIONABLE TABLET STRUCTURE

[75] Inventors: Michael K. Ullman; Stephen T. David; Claude E. Gallian, all of Evansville, Ind.

[73] Assignee: Mead Johnson & Company, Evansville, Ind.

[21] Appl. No.: 24,139

[22] Filed: Mar. 26, 1979

[51] Int. Cl.² ............................................. A61K 9/44
[52] U.S. Cl. ........................................ 424/15; D1/12
[58] Field of Search ............................ 424/15; D1/12

[56] References Cited

U.S. PATENT DOCUMENTS

| D. 89,941 | 5/1933 | Low | D1/12 |
|---|---|---|---|
| D. 91,644 | 3/1934 | Blackstone | D16/3 |
| D. 201,497 | 6/1965 | Ninger | D1/12 |
| D. 202,467 | 10/1965 | Guilmot | D1/12 |
| D. 216,307 | 12/1969 | Ninger | D1/12 |
| D. 220,956 | 12/1969 | Roberts | D16/3 |
| D. 228,456 | 9/1973 | Ninger | D1/12 |
| D. 229,049 | 11/1973 | Roberts | D1/12 |
| 1,836,604 | 12/1931 | Meyer | 127/30 |
| 2,052,376 | 8/1936 | Zellers | 424/15 |
| 3,336,200 | 8/1967 | Krause et al. | 424/15 |
| 3,723,614 | 3/1973 | Langauer | 424/15 |
| 3,883,647 | 5/1975 | Geller | 424/15 |

FOREIGN PATENT DOCUMENTS

| 1200790 | 9/1965 | Fed. Rep. of Germany . |
| 438385 | 5/1912 | France . |
| 352208 | 9/1937 | Italy . |
| 18888869 | of 1889 | United Kingdom . |
| 808014 | 1/1959 | United Kingdom . |
| 993291 | 5/1965 | United Kingdom . |

Primary Examiner—Shep K. Rose
Attorney, Agent, or Firm—R. E. Carnahan; R. H. Uloth

[57] ABSTRACT

The invention disclosed provides a multi-fractionable tablet structure initially configured in a unitary dosage while having readily severable sub-dosage units as components thereof. Score markings are positioned variously about the tablet both along the top and bottom surfaces of an approximately rectangular configuration whereas in preferred embodiments thereof, score markings additionally appear along opposite vertical side surfaces of the tablet. Special placement of the score markings readily permit at least either an accurate bisectional fracture or accurate trisectional fracture of the tablet as may be desired for patient consumption.

15 Claims, 18 Drawing Figures

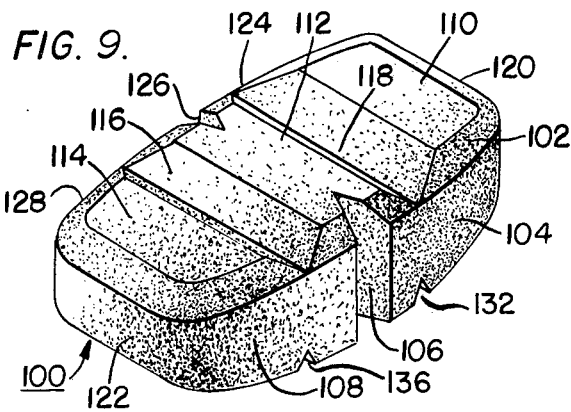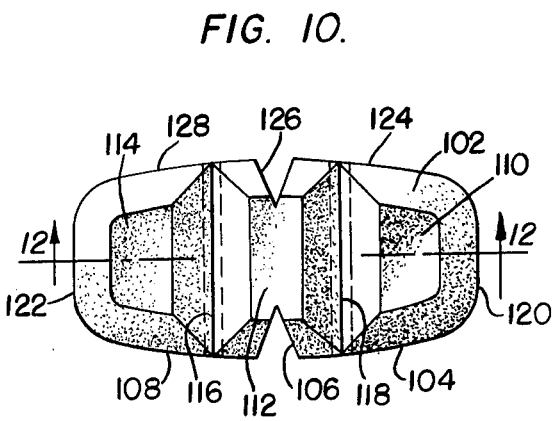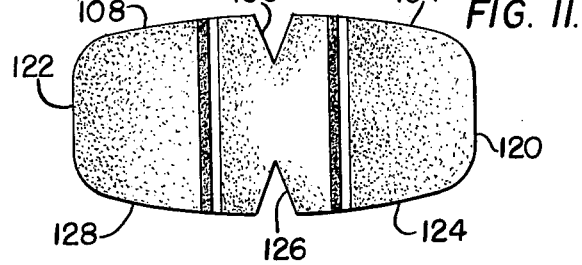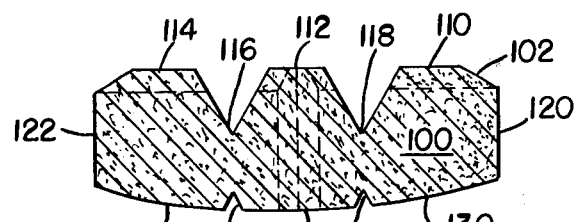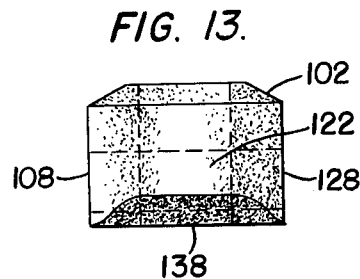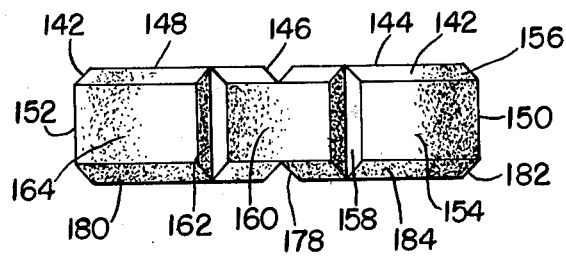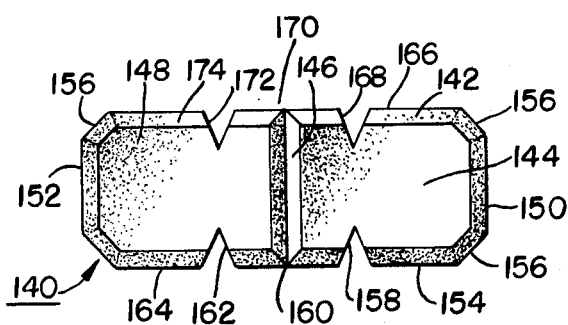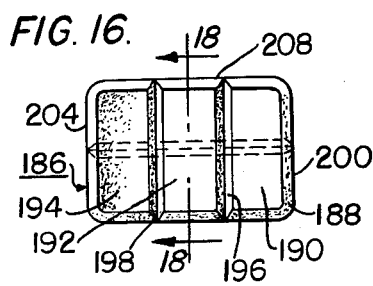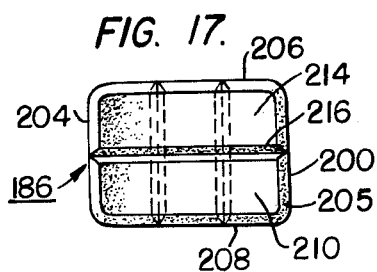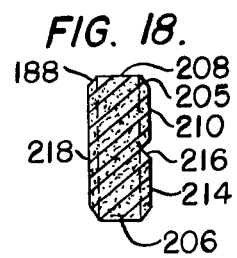

MULTI-FRACTIONABLE TABLET STRUCTURE

FIELD OF THE INVENTION

The present invention relates to a specially configurated multi-scored approximately rectangular tablet structure constituting a unitary dosage having readily severable sections which may be divided accurately and separated conveniently into at least either bisectional or trisectional sub-dosage units for patient consumption. The score markings are disposed specially along the top and bottom surfaces of the tablet structure whereas in preferred embodiments, score markings additionally appear along opposite vertical side surfaces of the tablet.

BACKGROUND OF THE INVENTION

It is well known in the pharmaceutical art that tablets may be formed with a groove or score marking to facilitate breakage of the tablet into sub-dosage units. Typically, these tablets are configurated circularly with a transverse score marking disposed along the top surface of the tablet such that the tablet may be severed into half-sections. One example of such a tablet is that disclosed by Geller, in U.S. Pat. No. 3,883,647. Another example of a tablet having surface score lines and a circular configuration except severable into quarter-sections is the maltese-cross scored tablet disclosed by Langauer in U.S. Pat. No. 3,723,614.

Because of the inherent difficulties of breaking a grooved tablet into accurate predetermined parts, a variety of diverse attempts have been made in the prior art seeking tablet structures which are readily fractured into sub-dosage units by application of moderate manual pressure. One example of such an attempt is that disclosed by Kraus et al, in U.S. Pat. No. 3,336,200, where two half sections having a highly tapered top surface which join at a score line positioned along the tablet's diameter. These diverse attempts to improve the convenience and accuracy of breaking a grooved tablet into predetermined parts have achieved limited success as best.

Inherently, the problem of breaking a grooved circular tablet resides in the hardness factor which results from tablet forming presses coupled with the small size configuration which does not allow for either ease of handling or breaking. A typical attempt to sever such circular tablet is by means of a sharp knife or related instrument which results more often than not, in fracture of the tablet into undesired miniature pieces. In cases where the severing into two pieces is successful, the pressure which is required along the score marking frequently propels both sections from the initial location unless extreme care is used to contain the two pieces during the breaking operation.

In order to overcome the problem of breaking circular tablets because of the hardness factor and small size, prior art attempts have also been made to configurate oblong tablets having score lines disposed transversely along the top surface. One example of such a tablet is that disclosed by Zellers in U.S. Pat. No. 2,052,376. These oblong tablet configurations have also realized limited success in providing a solution to a readily, accurately severable unitary dosage tablet into sub-dosage units. Also, although tablets such as those disclosed by Zellers are oblong in appearance, the transverse cross-sectional configuration thereof is typically cylindrical. This configuration invites disadvantages associated with inclusion of sufficient amounts of active ingredients in a configuration which may be readily consumed without suffering patient discomfort.

One of the well recognized advantages of having a readily dividable tablet is that it permits the administration of a plurality of sub-dosage units thereby avoiding costs for specially preparing an individual tablet for each dosage unit. Also, active ingredients are rendered more highly stable in larger dosage units and correspondingly the useful self-life for larger dosage units is extended significantly beyond that for the smaller individual dosage units.

It has now been found that by practice of the present invention, unitary dosage tablets may be prepared having specially disposed score markings which permit breakage of the unitary dosage tablet into at least either bisectional or trisectional equivalent sub-dosage units in a convenient accurate manner. Thus, a number of the disadvantages inherent in prior art attempts to provide a solution to tablet breakage into accurate sub-dosage units which may be conveniently consumed by a patient have now been overcome by practice of the present invention.

SUMMARY OF THE INVENTION

The present invention generally stated provides a new improved multi-scored tablet constituting a unitary dosage having readily severable sections which may be divided accurately and separated conveniently into at least either bisectional or trisectional sub-dosage units.

Generally, tablets of the present invention have score markings disposed along top and bottom surfaces of an approximately rectangular tablet configuration.

In one general embodiment, the present multi-fractionable tablet has an approximate rectangular configuration with two transverse score markings roughly equally positioned along both the top and bottom surfaces with intermediately disposed score markings positioned along opposite or vertical side wall sections of the tablet.

In another general embodiment, the present multi-fractionable tablet has an approximate rectangular configuration with two vertical score markings roughly equally positioned along opposite vertical side wall sections of the tablet with intermediately disposed score markings positioned along both the top and bottom surfaces thereof.

In yet another general embodiment, the present multi-fractionable tablet has an approximate rectangular configuration with two transverse score markings disposed along the top surface thereof and defining approximately equal trisectional dosage units with a longitudinal score marking disposed along the bottom surface of the tablet and defining approximately equal bisectional dosage units.

It is an object of the present invention to provide a multi-fractionable tablet structure prepared in a unitary dosage amount and having score markings disposed such that the tablet may be conveniently fractured into at least either bisectional or trisectional dosage units as desired for patient consumption.

It is also an object of the present invention to provide a multi-fractionable tablet which may be readily prepared using conventional tablet forming presses, and yet provide a tablet having an approximately rectangular configuration with specially positioned score markings such that the unitary dosage tablet may be readily and conveniently fractured into at least either bisectional or trisectional dosage units as desired for patient consumption.

These and other objects and advantages of the present invention will become more readily apparent from the more detailed description of preferred embodiments taken in conjunction with the drawings wherein similar elements are identified by like numerals throughout the several views.

DESCRIPTION OF THE FIGURES

FIG. 9 is a perspective view of yet another embodiment multi-fractionable pharmaceutical tablet of the present invention;

FIG. 10 is a top elevational view of the pharmaceutical tablet of FIG. 9;

FIG. 11 is a bottom elevational view of the pharmaceutical tablet of FIG. 9;

FIG. 12 is a longitudinal cross-sectional view of the pharmaceutical tablet of FIG. 10 taken along sectional lines 12—12;

FIG. 13 is an end view of the pharmaceutical tablet of FIG. 10;

FIG. 14 is a top elevational view of yet another embodiment multi-fractionable pharmaceutical tablet of the present invention;

FIG. 15 is a front elevational view of the pharmaceutical tablet of FIG. 14;

FIG. 16 is a top elevational view of yet another embodiment pharmaceutical tablet of the present invention;

FIG. 17 is a bottom elevational view of the pharmaceutical tablet of FIG. 16; and FIG. 18 is a transverse cross-sectional view of the pharmaceutical tablet of FIG. 16 taken along sectional lines 18—18.

DETAILED DESCRIPTION OF PREFERRED EMBODIMENTS

Figure 1:
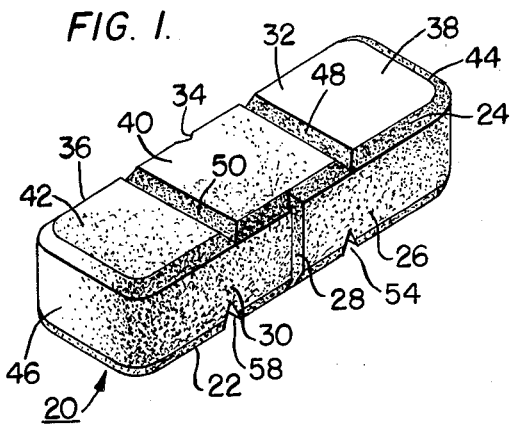
FIG. 1 is a perspective view of a multi-fractionable pharmaceutical tablet illustrating one embodiment of the present invention.
Figure 2:
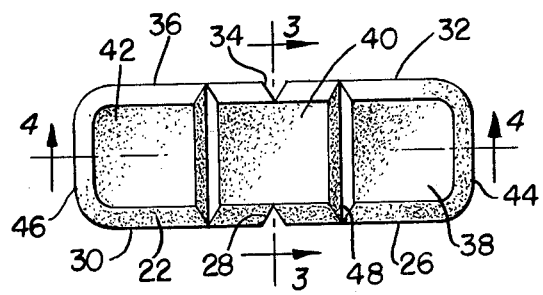
FIG. 2 is a top elevational view of the pharmaceutical tablet of FIG. 1.
Figure 3:
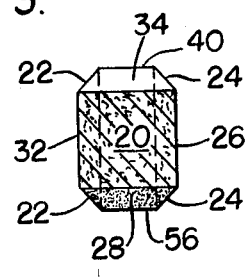
FIG. 3 is a transverse cross-sectional view of the pharmaceutical tablet of FIG. 2 taken along sectional lines 3—3.
Figure 4:
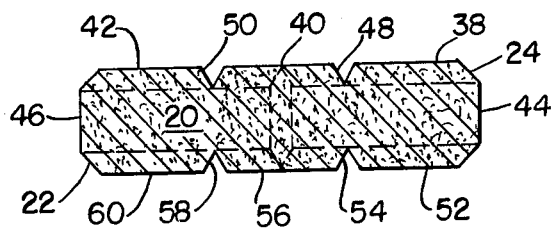
FIG. 4 is a longitudinal cross-sectional view of the pharmaceutical tablet of FIG. 2 taken along sectional lines 4—4.

FIGS. 1-4 illustrate pharmaceutical tablet 20 having bevel edge 22 disposed about the bottom peripheral edge thereof with bevel edge 24 disposed about the top peripheral edge. These bevel edges may vary as desired and typically range from about 25° to about 50° from the horizontal plane. One side of pharmaceutical tablet 20 is defined by vertical wall 26, intermediately disposed vertical score 28 and second vertical wall 30. Similarly, the opposite side of pharmaceutical tablet 20 is essentially the same configuration except defined by vertical wall 32, intermediately disposed vertical score 34, and second vertical wall 36. The end sections of tablet 20 are defined by vertical walls 44 and 46 respectively.

The top and bottom surfaces of pharmaceutical tablet 20 also approximately duplicate each other with the top surface defined by horizontal planar surface 38, intermediate horizontal planar surface 40 and second horizontal planar surface 42. The horizontal planar surface 38 is joined to the intermediate horizontal planar surface 40 by transversely disposed top score 48 whereas intermediate horizontal planar surface 40 is joined to the second horizontal planar surface 42 by transversely disposed second top score 50. Similarly, the bottom surface of pharmaceutical tablet 20 is defined by bottom horizontal planar surface 52 which joins transversely disposed bottom score 54 and bottom intermediate horizontal planar surface 56. This latter surface joins together a second transversely disposed bottom score 58 and second horizontal planar surface 60.

For consumption purposes, pharmaceutical tablet 20 may be administered as a unitary dosage. In the event a half dosage is desired, the tablet may be fractured conveniently along score markings 28-34, while one-third dosages may be administered by fracturing the tablet respectively along score markings 48-54 and 50-58. It will also be appreciated that a one-third dosage may be administered by fracturing the tablet along, for example, score markings 48-54, with the remaining two-third dosage unit being separately consumed.

Figure 5:
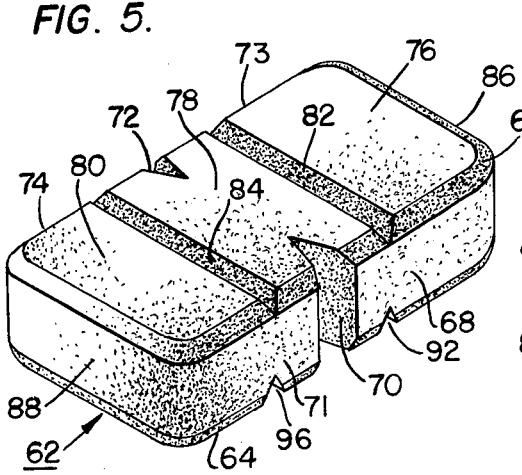
FIG. 5 is a perspective view of another embodiment multi-fractionable pharmaceutical tablet of the present invention.
Figure 6:
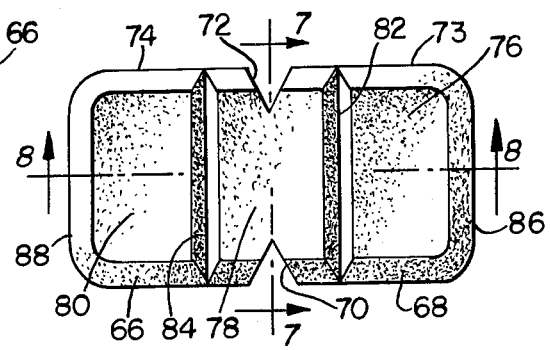
FIG. 6 is a top elevational view of the pharmaceutical tablet of FIG. 5.
Figure 7:
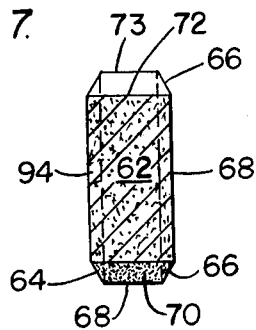
FIG. 7 is a transverse cross-sectional view of the pharmaceutical tablet of FIG. 6 taken along sectional lines 7—7.
Figure 8:
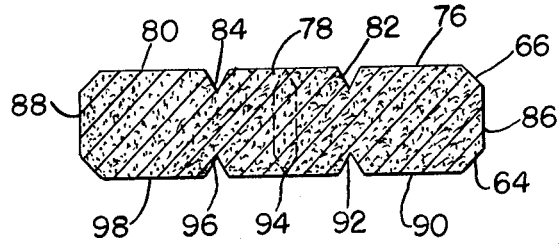
FIG. 8 is a longitudinal cross-sectional view of the pharmaceutical tablet of FIG. 6 taken along sectional lines 8—8.

FIGS. 5-8 illustrates an embodiment pharmaceutical tablet 62 of the present invention having bevel edge 64, similar to that of tablet 20, disposed about the bottom peripheral edge, with bevel edge 66 correspondingly positioned about the top peripheral edge. One side of pharmaceutical tablet 62 is defined by vertical wall 68, intermediately disposed vertical score 70 and second vertical wall 72. Similarly, the opposite side of pharmaceutical tablet 62 is essentially the same configuration except defined by vertical wall 70, intermediately disposed vertical score 72, and second vertical wall 74.

The essential distinction of the tablet structure 62 over the tablet structure 20 resides in the significant depth of the score markings 70-72. These score markings may be impressed to depths beyond the bevel edge as opposed to the score markings 28-34 which essentially project to the horizontal planar surface of the top and bottom portions of tablet 20. Score markings 70-72 may be at a V-groove angle of about 40° to 50°, and preferably about 45°, with each V-groove depth being about ¼ to about ⅓ the width of the tablet.

The top and bottom surfaces of pharmaceutical table 62 also approximately duplicate each other, with the top surface defined by horizontal planar surface 76, intermediate horizontal planar surface 78 and second horizontal planar surface 80. The horizontal planar surface 76 is joined to the intermediate horizontal planar surface 78 by transversely disposed top score 82, again similar to the corresponding score marking 48 of tablet 20, whereas intermediate horizontal planar surface 78 is joined to the second horizontal planar surface 80 by transversely disposed second top score 84. Similarly, the bottom surface of pharmaceutical tablet 62 is defined by bottom horizontal planar surface 90 which join transversely disposed bottom score 92 and bottom intermediate horizontal planar surface 94. This latter surface joins together a second transversely disposed bottom score 96 and second horizontal planar surface 98. The end walls of tablet 62 are defined by vertical walls 86 and 88 respectively.

Again, for consumption purposes, pharmaceutical tablet 62 may be administered as a unitary dosage. In the event a half dosage is desired, the tablet may be fractured conveniently along score markings 70–72, while one-third dosages may be administered by fracturing the tablet respectively along score markings 82–92 and 84–96. It will also be appreciated that a one-third dosage may be administered by fracturing the tablet along, for example, score markings 82–92, with the remaining two-thirds dosage unit being separately consumed.

FIGS. 9–12 illustrate an embodiment pharmaceutical tablet 100 of the present invention having bevel edge 102 disposed about only the top peripheral edge. One side of pharmaceutical tablet 100 is defined by arcuate vertical wall 104, intermediately disposed vertical score 106 and second arcuate vertical wall 108. Similarly, the opposite side of pharmaceutical tablet 100 is essentially the same configuration except defined by arcuate vertical wall 124, intermediately disposed vertical score 126, and second arcuate vertical wall 128. The end portions of tablet 100 appear as substantially vertical wall surfaces 120 and 122 respectively.

The vertical score markings 106 and 126 of tablet 100 are configured similar to score markings 70 and 72 of tablet 62. Correspondingly, the size and angle dimensions are similar for practical purposes of construction.

The top and bottom surfaces of pharmaceutical tablet 100 present a significant contrast in that the top surface is defined by horizontal planar surface 110, intermediate horizontal planar surface 112 and a second horizontal planar surface 114. The horizontal planar surface 110 is joined to the intermediate horizontal planar surface 112 by transversely disposed top score 118, whereas intermediate horizontal planar surface 112 is joined to the second horizontal planar surface 114 by transversely disposed second top score 116.

Score markings 116 and 118 are deeply grooved indentations having a V-groove angle of about 55° to about 65°, with an angle of about 60° being preferred. The depth of these V-grooves may vary from about ¼ to about ⅜ of the thickness of the tablet.

The bottom surface of pharmaceutical tablet 100 is defined by a slightly arcuate surface 130 which joins transversely disposed bottom score 132 and bottom intermediate surface 134. This latter surface joins together a second transversely disposed bottom score 136 and second slightly arcuate surface 138.

The V-groove score markings 132 and 136 vary from an angle of about 55° to about 65° with about 60° being preferred. However, and significantly, score markings 132 and 136 only slightly indent into the bottom surface of tablet 100. Typically, this depth varies from about ¼ to about ⅓ of the thickness of this tablet.

For consumption purposes, pharmaceutical tablet 100 may be also administered as a unitary dosage. In the event a half dosage is desired, the tablet may be fractured conveniently along score markings 106–126, while one-third dosages may be administered by fracturing the tablet respectively along score markings 118–132 and 116–136. It will also be appreciated that a one-third dosage may be administered by fracturing the tablet along, for example, score markings 118–132, with the remaining two-third dosage unit being separately consumed.

FIGS. 14–15 illustrate yet another embodiment pharmaceutical tablet 140 which approximates the configuration of tablet 62 except the correspondingly defined top and side score markings are shifted 90 degrees to the side and bottom surfaces respectively. The remaining bottom and opposite side score markings are also transposed that same extent.

Pharmaceutical tablet 140 includes bevel edge 142 disposed about the top peripheral edge thereof, also similar in configuration to the bevel edge 24 of tablet 20.

The top and bottom surfaces of pharmaceutical tablet 140 have correspondingly configured surfaces in that the top surface is defined by horizontal planar surface 144, and a second horizontal planar surface 148. The horizontal planar surface 144 is joined to the second horizontal planar surface by transversely disposed top score 146.

The front and rear surfaces of pharmaceutical tablet 140 also approximately duplicate each other with the front surface defined by vertical surface 154, intermediate vertical surface 160 and second vertical surface 164. The vertical surface 154 is joined to the intermediate vertical surface 160 by score marking 158, whereas intermediate vertical surface 160 is joined to the second vertical surface 164 by second score marking 162. Similarly, the opposite side surface of pharmaceutical tablet 140 is defined by vertical surface 166 which joins first score marking 168, and intermediate vertical surface 170. This latter surface joins together a second score marking 172 and second vertical surface 174.

The corner edges of tablet 140 may also be tapered as desired such as elements 156 illustrating a taper of approximately 45 degrees.

Score markings 158, 162, 168 and 172 are all correspondingly configured with V-grooves having an approximate V-angle of about 40 to about 50 degrees, with an angle of about 45 degrees being preferred, with each V-groove depth being about ¼ to about ⅓ the thickness of the tablet.

Score markings 146 and 178 may be configured similarly to the related score markings 82 of the tablet 62.

The dosages which may be extracted using tablet 140 approximately correspond to that of tablet 62 except, however, accounting for the 90 degree transposition of surfaces.

FIGS. 16–18 illustrate pharmaceutical tablet 186 having bevel edge 188 disposed about the upper peripheral edge thereof with bevel edge 205 disposed about the bottom peripheral edge. These bevel edges may vary as desired and typically range from about 25° to about 50° from the horizontal plane. One side of pharmaceutical tablet 186 is defined by vertical wall 200 whereas the opposite side is defined by vertical wall 204. In similar regard, the front surface of tablet 186 is defined by vertical wall 206 whereas the oppositely disposed rear portion is defined by vertical wall 208.

The top surface of pharmaceutical tablet 186 is uniquely distinct from the bottom thereof. The top surface is defined by horizontal planar surface 190, intermediate horizontal planar surface 192 and second horizontal planar surface 194. Planar surface 190 is joined to the intermediate horizontal planar surface 192 by means of score marking 196, whereas the intermediate planar surface 192 is joined to the second horizontal planar surface 194 by means of second score marking 198.

The bottom surface of pharmaceutical tablet 186 is defined by a first bottom planar surface 210, joined by a longitudinally disposed score marking 216 to a second bottom planar surface 214.

Score markings 196, 198 and 216 may have similar V-groove configurations and for constructions purposes, are similarly configured to score markings 48 and 50 of tablet 20.

For consumption purposes, pharmaceutical tablet 186 may be administered as a unitary dosage. In the event a half dosage is desired, the tablet may be fractured conveniently along score marking 216, while one-third dosages may be administered by fracturing the tablet respectively along score markings 196 and 198. It will also be appreciated that further sub-dosage units may be administered by fracturing the tablet along, for example, score markings 196, 198 as well as 216.

The present multi-fractionable tablet structure includes specially positioned score markings for either at least an accurate bisectional fracture of the tablet or accurate trifunctional fracture. It will be apparent that with the same convenience, positioning of the score markings may permit fracture of pharmaceutical tablet 186 into as many as six substantially equivalent dosages. Correspondingly, the remaining pharmaceutical tablets, namely, 20, 62, 100 and 140 may be fractured readily into two pairs of equivalent dosages with, for example, fracture along score markings 48–54 and score markings 50–58 of pharmaceutical tablet 20 defining one pair of dosage units with further fracture along score markings 28–34 defining the second pair of dosage units.

Tablets of the present invention may be composed of a variety of ingredients such as one or more active pharmaceutical ingredients, fillers, lubricants, carriers, flavoring ingredients or the like as desired. These materials are well known to skilled tablet formulators.

Although it has not been specially disclosed herein, it will be appreciated that the present multi-fractionable tablet structure may be specially marked with a corporate logo or otherwise colored as desired to reflect particular dosage units being consumed. Also, the present tablet may be coated with suitable materials well known in the tablet formation art.

Having described the present invention with particular reference to the disclosed embodiments, it will be obvious to those skilled in this art, that various changes and modifications may be made therein without departing from the spirit and scope of the invention which is disclosed and claimed herein.

What is claimed is:

1. A tablet structure which comprises, an approximately rectangularly-shaped unitary body having oppositely disposed first and second planar surfaces being joined respectively by oppositely disposed vertical end walls relative to a front wall surface and a rear wall surface; said planar surfaces each containing two transverse score markings approximately oppositely positioned and defining approximately equal trisectional dosage units; said front and rear wall surfaces each containing one vertical score marking; each of said vertical score markings being disposed intermediate said two transverse score markings and approximately opposite to each other; whereby the unitary body may be fractured into at least bisectional or trisectional units for consumption.

2. The tablet structure of claim 1 wherein the planar surfaces include bevel edges, and wherein the score markings have an indentation depth to a line defining the bevel edge.

3. The tablet structure of claim 2 wherein the bevel edges range from about 25 degrees to about 50 degrees from the horizontal plane.

4. The tablet structure of claim 3 wherein the bevel edge angle is about 30 degrees to about 45 degrees.

5. The tablet structure of claim 1 wherein the vertical score markings have a V-groove angle of about 40 degrees to about 50 degrees, with a V-groove depth being about ¼ to about ⅓ the width of the tablet.

6. The tablet structure of claim 1 wherein the planar surfaces define the top and bottom surfaces respectively.

7. The tablet structure of claim 1 wherein the planar surfaces define front and rear surfaces respectively.

8. The tablet structure of claim 1 wherein said vertical score markings disposed intermediate said two transverse score markings are deeply grooved indentations having a V-groove angle of about 40 degrees to about 50 degrees with a V-groove depth of about ¼ to about ⅓ the width of the tablet.

9. The tablet structure of claim 8 wherein the score angle is about 45 degrees.

10. The tablet structure of claim 1 wherein two transverse score markings disposed along one planar surface are deeply grooved indentations having a V-groove angle of about 55 degrees to about 65 degrees, with a V-groove depth of about ¼ to about ⅜ of the thickness of the tablet.

11. The tablet structure of claim 9 wherein the planar surface opposite that having deeply grooved indentations is arcuate, and wherein the V-groove angle is about 60 degrees.

12. A tablet structure which comprises, an approximately rectangularly-shaped unitary body oppositely disposed first and second planar surfaces, said first and second planar surfaces being joined respectively by oppositely disposed vertical end walls relative to a front wall surface and a rear wall surface; one of said planar surfaces having two transverse score markings defining approximately equal trisectional dosage units; the second planar surface having one longitudinal score marking defining approximately equal bisectional dosage units; whereby the unitary body may be fractured into at least bisectional or trisectional dosage units for consumption.

13. The tablet structure of claim 12 wherein the planar surfaces include bevel edges, and wherein the score markings have an indentation depth to a line defining the bevel edge.

14. The tablet structure of claim 13 wherein the bevel edges range from about 25 degrees to about 50 degrees from the horizontal plane.

15. The tablet structure of claim 13 wherein the bevel edge angle is about 30 degrees to about 45 degrees.

* * * * *